(12) United States Patent
Hill et al.

(10) Patent No.: US 6,770,052 B2
(45) Date of Patent: *Aug. 3, 2004

(54) WET/DRY AUTOMATIC INJECTOR ASSEMBLY

(75) Inventors: Robert L. Hill, Abington, MD (US); John G. Wilmot, Mount Airy, MD (US); Steven Griffiths, Ellicott City, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 70 days.

This patent is subject to a terminal disclaimer.

(21) Appl. No.: 09/972,202

(22) Filed: Oct. 9, 2001

(65) Prior Publication Data

US 2002/0049407 A1 Apr. 25, 2002

Related U.S. Application Data

(60) Provisional application No. 60/238,458, filed on Oct. 10, 2000.

(51) Int. Cl.[7] ........................ A61M 37/00; A61M 5/00
(52) U.S. Cl. ........................ 604/89; 604/191; 604/190
(58) Field of Search ................ 604/82, 89–92, 604/191, 218, 236, 238, 187, 87, 88, 190, 200–202

(56) References Cited

U.S. PATENT DOCUMENTS

| | | | |
|---|---|---|---|
| 3,757,779 A | | 9/1973 | Rovinski |
| 3,863,624 A | * | 2/1975 | Gram ........................ 604/191 |
| 4,043,335 A | | 8/1977 | Ishikawa |
| 4,060,082 A | | 11/1977 | Lindberg et al. |
| 4,306,554 A | | 12/1981 | Schwartz et al. |
| 4,529,403 A | | 7/1985 | Kamstra |

(List continued on next page.)

FOREIGN PATENT DOCUMENTS

| | | |
|---|---|---|
| DE | 1 961 166 | 7/1970 |
| EP | 0 112 574 | 7/1984 |
| EP | 0 361 668 | 4/1990 |
| EP | 0 405 320 A2 | 1/1991 |
| EP | 0 511 183 A1 | 10/1992 |
| FR | 2 604 363 | 4/1988 |
| FR | 2 741 810 | 6/1997 |
| WO | WO 94/09839 | 5/1994 |
| WO | WO96/01135 | 1/1996 |
| WO | WO01/93925 | 12/2001 |

OTHER PUBLICATIONS

A copy of the PCT Search Report dated May 3, 2002, issued in related PCT Application No. PCT/US01/42593.

A copy of the PCT Search Report dated May 3, 2002, issued in related PCT Application No. PCT/US01/42594.

A copy of the PCT Search Report dated May 3, 2002, issued in the corresponding PCT Application No. PCT/US01/42595.

Primary Examiner—Sharon Kennedy
(74) Attorney, Agent, or Firm—Pillsbury Winthrop LLP

(57) ABSTRACT

The present invention is directed to an automatic injection device containing a pre-loaded charge of medicament for automatically self-administering the medicament upon actuation thereof. The automatic injection device includes a housing assembly having an interior chamber, a filter assembly, an activation assembly and a needle assembly. In accordance with the present invention, the interior chamber may include a dry compartment for storing a predetermined dry charge of dry medicament therein, and a wet compartment for storing a predetermined amount of liquid injection solution therein. The filter assembly enhances the laminar flow of fluid between the wet compartment to the dry compartment prior to the pressurization of the liquid injection solution within the wet compartment.

24 Claims, 2 Drawing Sheets

U.S. PATENT DOCUMENTS

| | | | |
|---|---|---|---|
| 4,599,082 A | | 7/1986 | Grimard |
| 4,755,169 A | | 7/1988 | Sarnoff et al. |
| 4,898,580 A | * | 2/1990 | Crowley .................... 604/90 |
| 5,015,229 A | * | 5/1991 | Meyer et al. ................ 604/90 |
| 5,298,024 A | | 3/1994 | Richmond |
| 5,429,603 A | * | 7/1995 | Morris ........................ 604/88 |
| 5,472,422 A | | 12/1995 | Ljungquist |
| 5,704,918 A | | 1/1998 | Higashikawa |
| 5,807,344 A | * | 9/1998 | Iwasake ..................... 604/190 |
| 5,971,953 A | * | 10/1999 | Bachynsky ................. 604/90 |
| 6,093,172 A | | 7/2000 | Funderburk et al. |
| 6,149,628 A | | 11/2000 | Szapiro et al. |
| 6,379,328 B1 | | 4/2002 | Mac Clay |
| 2002/0049407 A1 | | 4/2002 | Hill et al. |

* cited by examiner

WET/DRY AUTOMATIC INJECTOR ASSEMBLY

CROSS REFERENCE TO RELATED APPLICATION

This application claims priority from U.S. Provisional Serial No. 60/238,458, filed Oct. 10, 2000, and is incorporated herein in its entirety by reference

FIELD OF THE INVENTION

The present invention relates to automatic injectors for delivering medicament to an injection site. In particular, the present invention is directed to an automatic injector assembly for quickly combining a liquid material with a dry material to form a liquid medicament for delivering the medicament to an injection site. In accordance with the present invention, the automatic injector assembly includes a separation filter assembly that keeps the liquid material separated from the dry material until the automatic injector assembly is activated.

BACKGROUND OF THE INVENTION

An automatic injector is a device for enabling an individual to self-administer a dosage of medicament into his or her flesh. The medicament is usually stored in liquid form. The advantage of automatic injectors is that they contain a measured dosage of a liquid medicament in a sealed sterile cartridge and can be utilized for delivering the medicament into the flesh during emergency situations. Another advantage of automatic injectors is that the self-administration of the medicament is accomplished without the user initially seeing the hypodermic needle through which the medicament is delivered and without having the user to manually force the needle into his or her own flesh.

There are drawbacks associated with the storage of medicament in liquid form. Some medicaments are not stable in liquid form. Furthermore, some liquid medicaments typically have a shorter shelf life than their solid counterparts. Others have developed automatic injectors that store the medicament in solid form and a liquid injection solution. These injectors, disclosed for example in U.S. Reissue Pat. No. 35,986, entitled "Multiple Chamber Automatic Injector," (the disclosure of which is incorporated herein specifically by reference), however, require the user of the injector to expedite dissolution of the solid component by manually shaking the liquid component and the solid component immediately prior to injection. This increases the time needed to administer a dose of medicament. Furthermore, the improper mixing of the medicament with the liquid injection solution may release an insufficient dose of medicament. There is a need for an automatic injector that stores medicament in solid form that does not require manual premixing by the user. Furthermore, rapid delivery of the medicament is needed for emergency medical situations (e.g. nerve gas and chemical agent poisoning).

OBJECTS OF THE INVENTION

It is therefore an object of the present invention to provide an automatic injector device that stores medicament in a solid form for increased shelf life.

It is another object of the present invention to provide an automatic injector device that automatically mixes a solid medicament with a liquid injection solution upon activation.

It is another object of the present invention to provide an automatic injector device having a separation filter assembly that separates the solid medicament from the liquid injection solution until the injector is activated.

It is another object of the present invention to provide an automatic injector device having a filter assembly that provides for a more laminar flow of the liquid injection solution into the dry medicament to assist in the dissolution of the dry medicament into the liquid injection solution.

It is another object of the present invention to provide a wet/dry automatic injector device with a solid medicament support within the device to prevent the passage of undissolved solid medicament to the needle assembly of the injector assembly thereby preventing blockage of the needle.

Additional objects and advantages of the invention are set forth, in part, in the description which follows, and, in part, will be apparent to one of ordinary skill in the art from the description and/or practice of the invention.

SUMMARY OF THE INVENTION

In response to the foregoing challenges, applicants have developed an innovative automatic injection device having both wet and dry storage compartments. The present invention is directed to an automatic injection device containing a pre-loaded charge of medicament for automatically self-administering the medicament upon actuation thereof. The automatic injection device includes a housing assembly having an interior chamber, a filter assembly, an activation assembly and a needle assembly. In accordance with the present invention, the interior chamber may include a dry compartment for storing a predetermined dry charge of dry medicament therein, and a wet compartment for storing a predetermined amount of liquid injection solution therein.

The filter assembly is positioned between the dry compartment from the wet compartment. The filter assembly creates a laminar fluid flow of liquid injection solution as the solution passes from the wet compartment to the dry compartment. This improves dissolution of the dry medicament in the liquid injection solution.

The automatic injector in accordance with the present invention includes a plunger assembly positioned adjacent the filter assembly. The plunger assembly is adapted to prevent the transfer of the liquid injection solution from the wet compartment to the dry compartment prior to pressurization of the liquid injection solution within the wet compartment. In accordance with one embodiment of the present invention, the plunger assembly may include a passageway for transferring the liquid injection solution from the wet compartment to the dry compartment and a membrane assembly for preventing the transfer of the liquid injection solution from the wet compartment to the dry compartment prior to the pressurization of the liquid injection solution within the wet compartment. The membrane is designed to rupture upon pressurization of the wet compartment. In accordance with another embodiment of the present invention, the plunger assembly is adapted to moves from a first position to a second position during the pressurization of the liquid injection solution within the wet compartment. This movement opens a fluid passageway between the plunger assembly and the interior chamber to permit the passage of the liquid injection fluid from the wet compartment to the dry compartment.

The activation assembly pressurizes the liquid injection solution in the wet compartment, which causes the liquid injection solution in the wet compartment to be transferred to the dry compartment. The dry medicament dissolves in the liquid injection solution as the liquid injection solution passes through the dry compartment. It is contemplated that at least a portion of a plunger assembly of the activation assembly may contact the plunger assembly adjacent the filter assembly, which moves the filter and plunger assembly towards the needle assembly to force the remaining liquid injection solution and the dry medicament through the needle assembly.

The automatic injection device may further include a dry medicament support structure located within the interior chamber. The support structure prevents undissolved dry medicament from entering the needle assembly.

BRIEF DESCRIPTION OF THE DRAWINGS

The invention will be described in conjunction with the following drawing in which like reference numerals designate like elements and wherein.

DETAILED DESCRIPTION OF THE INVENTION

Figure 1:
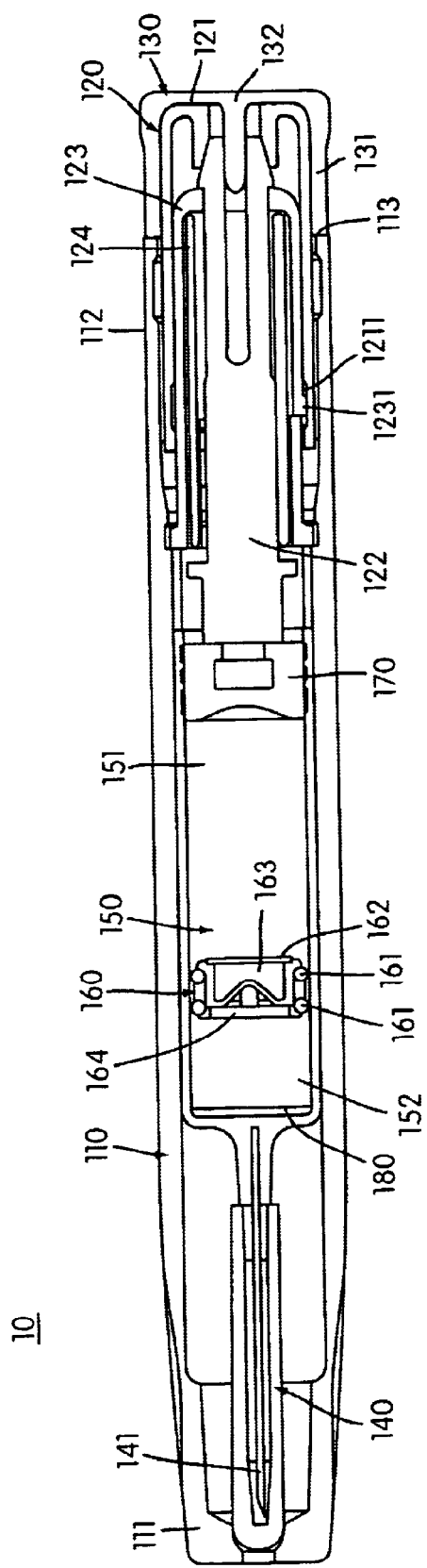
FIG. 1 is a cross-sectional side view of a wet/dry automatic injector assembly in accordance with an embodiment of the present invention.

Referring now, more particularly to the figures, there is shown in FIG. 1 an automatic injector assembly 10 in accordance with an embodiment of the present invention. The present invention is described in connection with a push button type auto injector, whereby the user removes an end cap assembly and presses a button to trigger the injection process. The present invention, however, is not limited to push button type automatic injectors; rather, it is contemplated that the present invention may be incorporated into a nose activated auto injector, as described for example in U.S. Pat. No. 5,658,259. The disclosures of which are hereby specifically incorporated herein by reference. It is further contemplated that the present invention may be incorporated into a syringe assembly.

The automatic injector assembly 10 includes a generally hollow housing 110. The housing 110 includes an injection insertion end 111 and an activation end 112, as shown in FIG. 1. An actuator assembly 120 extends from an opening 113 in the activation end 112 of the housing 110. The actuator assembly 120 is slidably received within the housing 110. A removable end cap assembly 130 is releasably secured to the actuator assembly 120. When the end cap assembly is secured to the actuator assembly 120, a side portion 130 of the end cap assembly is adapted to abut the housing 110 to prevent movement of the actuator assembly 120 and unintentional injection of the medicament.

The actuator assembly 120 includes a push button actuator assembly 121 having a hollow interior. The end cap assembly engages the push button actuator assembly 121. A collet 122 is located within the hollow interior of the push button actuator assembly 121. An inner tube 123 is also located within the hollow interior of the push button actuator assembly 121. The inner tube 123 is adapted to contact the collet 122, as shown in FIG. 1. An opposite end of the inner tube 123 may include an engagement rib 1231 that is adapted to be received within a complementary recess 1211 within the push button actuator assembly 121. A drive assembly 124 is positioned within a space formed between the collet 122 and the inner tube 123. A pin 132 extends from the end cap assembly 130 and is received within the collet 122 to prevent or block the collet 122 from collapsing prior to activation.

The user removes the end cap assembly 130. The pin 132 no longer prevents movement of the collet 122. Upon depression of the actuator assembly 121, the drive assembly 124 provides the necessary force when activated to operate the injector 10 to inject the user with a necessary dosage of medicament. It is contemplated that the drive assembly 124 may be a spring assembly, a compressed gas assembly or any other suitable energy storing device. When activated, the drive assembly 124 causes the collet 122 to move such that a needle assembly 140 extends from an opening in the injection end 111 of the housing 110. Movement of the collet 122 also causes mixing of the dry medicament with the liquid injection solution, described in greater detail below.

Located within the interior of the housing 110 is a chamber 150 for housing both the liquid injection solution and the dry medicament. The liquid injection solution is located within a wet portion 151 of the chamber 150. The dry medicament is located within a dry portion 152 of the chamber 150. It is contemplated that the dry medicament may be in either powder or freeze-dried form. A separation filter assembly 160 separates the dry portion 152 from the wet portion 151. The separation filter assembly 160 provides a seal to prevent seepage of the liquid injection solution into the dry portion 152 prior to activation of the injector assembly. The separation filter assembly 160 includes at least one sealing assembly 161 located around the perimeter of the filter assembly 160. Each sealing assembly 161 engages the wall of the chamber 150.

The separation filter assembly 160 may include an optional membrane assembly 162. The membrane assembly 162 is designed to burst in response to build up of pressure within the wet portion 151 of the chamber 150 in response to movement of the collet 122. The liquid injection solution enters an interior cavity 163 within the separation filter assembly 160 and passes through a filter 164. The liquid injection solution then enters the dry portion 152 of the chamber 150 where it mixes with and dissolves the dry medicament. The material forming the filter 164 produces the laminar flow of the liquid injection solution. The filter 164 may include a series of channels and ribs to uniformly distribute the liquid injection solution into the dry portion 152 for mixing the dry medicament.

One end of the collet 122 extends into the wet portion 151 of the chamber 150 within the housing 110. A plunger assembly 170 is secured to the end of the collet 122, as shown in FIG. 1. The plunger assembly 170 is adapted to engage the side wall of the wet portion 151 to prevent leakage of the contents (e.g. liquid injection solution) of the wet portion 151 from the activation end 112 of the housing 110. The plunger assembly 170 is preferably formed from a material having low frictional properties such that the collet 122 and plunger assembly 170 may easily slide within the wet portion 151 when operated. Alternatively, the plunger assembly 170 may be lubricated with silicon or other suitable non reactive lubricant. The movement of the collet 122 and the plunger assembly 170 pressurizes the liquid injection solution located within the wet portion 151.

Upon activation of the push button actuator assembly 121, the collet 122 and plunger assembly 170 advance within the wet portion 151 of the chamber 150 toward the separation filter assembly 160. In response to a sufficient amount of pressure within the wet portion 151, the membrane assembly 162 ruptures and the liquid injection solution travels through the separation filter assembly 160 into the dry portion 152 to mix with the dry medicament, as described above. The mixture of the liquid injection solution and the dry medicament then exits the dry portion 152 through the injection needle 141 of the needle assembly 140.

The high pressure developed within the wet portion 151 in response to movement of the collet 122 and the plunger assembly 170 forces the liquid injection solution through the separation filter assembly 160 dissolving the drug into a solution which will continue to be forced out through the needle assembly 140. The collet 122 and plunger assembly 170 will eventually contact the separation filter assembly 160, which causes the separation filter 160 to move in the direction of the needle assembly 140. This action causes the remaining solution within the wet portion 151 and the dry portion 152 to be dispersed through the needle assembly 140, which reduces the amount of residual dry medicament remaining within the chamber 150. A filter assembly or powder support assembly 180 may be located adjacent the needle assembly 140 to prevent any undissolved medicament from entering the needle assembly 140.

As discussed above, the movement of the collet 122 and drive assembly 124 causes the injection needle 141 of the injection assembly 140 to advance and protrude through the housing 110. The injection of the medicament can be performed with a simple operation. The user simply removes the end cap assembly, locates the injection end of the housing 110 adjacent the injection site and presses the push button actuator assembly 121. This operation automatically triggers the operation of the drive assembly 124 to advance the collet 122 causing the liquid injection solution located within the wet portion 151 to enter the dry portion 152 through the separation filter assembly 160. The dissolved medicament is then transmitted through the injection needle 141 to provide the user with the necessary dose of medicament. The automatic injector 10 in accordance with the present invention reduces the amount of time required to administer medicament compared to other wet/dry injectors. The present invention eliminates the need for mixing by the user.

Figure 2:
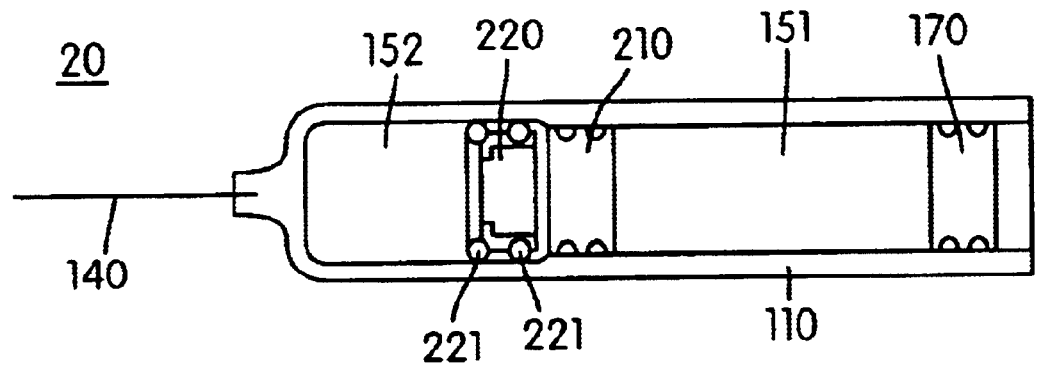
FIG. 2 is a partial cross sectional side view of a wet/dry automatic injector assembly in accordance with another embodiment of the present invention, wherein the by-pass plunger is in a closed position blocking the flow of the liquid injection solution.
Figure 3:
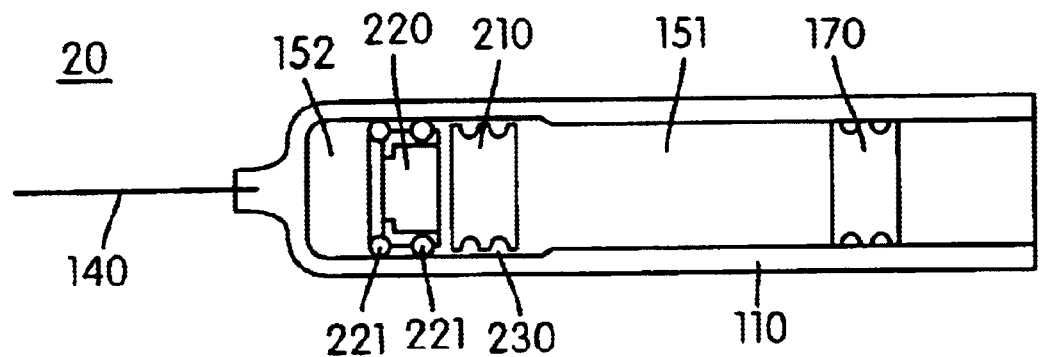
FIG. 3 is a partial cross sectional side view of the wet/dry automatic injector assembly of FIG. 2, wherein the by-pass plunger is in an open position permitting the flow of the liquid injection solution.

An automatic injector assembly 20 in accordance with another embodiment of the present invention will now be described in connection with FIGS. 2 and 3. The automatic injector assembly 20 includes a by-pass plunger assembly. The injector assembly 20 has substantially the same construction as the injector assembly 10 with the exception of the provision of a by-pass plunger assembly 210 and movable filter assembly 220. The movable filter assembly 220 includes at least one sealing assembly 221, which engages the wall of the dry portion 152 of the chamber 150. The by-pass plunger assembly 210 is positioned adjacent one end of the wet portion 151 of the chamber 150. A filter assembly 220 is positioned adjacent the plunger assembly 210 in the dry portion 152 of the chamber 150, as shown in FIG. 2. In accordance with this embodiment of the present invention, the dry portion 152 has a larger diameter than the wet portion 151. During operation, as the plunger 170 is moved toward the needle assembly 140, the by-pass plunger assembly 210 is moved into the dry portion 152 of the chamber, which opens a fluid passageway 230 between the wet and dry portions of the chamber 150, as shown in FIG. 3. The liquid injection solution flows through the filter assembly 220. Like the filter assembly 164, the filter assembly 220 creates a laminar flow of the injection solution as it flows through the filter. This enhances the dissolution of the dry medicament in the liquid injection solution.

It is contemplated that the fluid passageway 230 may be formed by a series of by-pass slots, ribs on the container that distort the second plunger assembly or any other assembly that is capable of permitting the flow of liquid injection solution around the by-pass plunger assembly 210.

It will be apparent to those skilled in the art that various modifications and variations may be made without departing from the scope of the present invention. For example, it is contemplated that a cover assembly, described for example in U.S. Pat. No. 5,295,965 (the disclosure of which is specifically incorporated herein by reference) may be secured to the injection end of the housing 110 after deployment of the medicament. Furthermore, the automatic injector may further include a nipple plunger assembly, as described for example in U.S. Pat. No. 5,465,727 (the disclosure of which is specifically incorporated herein by reference). Thus, it is intended that the present invention covers the modifications and variations of the invention, provided they come within the scope of the appended claims and their equivalents.

What is claimed is:

1. An automatic injection device containing a pre-loaded charge of medicament for automatically self-administering the medicament upon actuation thereof, the device comprising:

a housing assembly having an interior chamber, the interior chamber including a dry compartment containing a dry medicament component, and a wet compartment containing a liquid component to be mixed with the dry component;

a seal structure between the dry compartment and the wet compartment, the seal structure being initially in a sealing condition that maintains the dry component sealed from the wet component, the seal structure being converted to a mixing condition as a result of activation of the device;

a fluid distributing member disposed between the liquid component and the dry medicament component;

a needle assembly that dispenses the charge of medicament from the housing;

an activation assembly carried by the housing and including a stored energy source, wherein activation of the activation assembly releases the stored energy from the stored energy source, and wherein the release of the stored energy causes a) the seal structure to be converted from the sealing condition to the mixing condition and thereby permit the liquid component to pass there through, b) the liquid component to be forced through the fluid distributing member and distributed to the dry component and facilitate mixing and dissolution of the dry medicament component in the liquid component, and c) force the mixed liquid and dry components through the needle assembly.

2. An automatic injection device according to claim 1, wherein the fluid distributing member comprises a filter.

3. An automatic injection device according to claim 1, wherein the seal structure comprises a sealing assembly and a burstable membrane carried by the sealing assembly.

4. An automatic injection device according to claim 3, wherein the sealing assembly has an outer periphery that forms a peripheral seal with an interior wall of the interior chamber, and an inner seal portion spaced radially inward from the peripheral seal that seals a passage formed in the seal structure.

5. An automatic injection device according to claim 1, wherein the activation assembly includes a pre-compressed spring.

6. An automatic injection device according to claim 1, wherein the seal structure and the distributing member are integrated into a single assembly.

7. An automatic injection device according to claim 1, wherein the needle assembly is disposed toward a forward end of the housing assembly and the activation assembly is disposed toward a rearward end of the housing assembly, wherein the dry medicament component is disposed forwardly of the liquid component.

8. An automatic injection device according to claim 7, wherein the activation assembly includes a pre-compressed spring that urges a collet rod forwardly through the housing, and wherein forward movement of the collet rod creates sufficient pressure on the liquid component to cause the liquid component to force the seal structure into the mixing condition.

9. An automatic injection device according to claim 8, further comprising a dry medicament support structure disposed between the dry medicament component and the needle assembly.

10. An automatic injection device according to claim 8, wherein the seal structure incorporates a burstable membrane.

11. An automatic injection device according to claim 8, wherein the seal structure is movable forwardly with respect to the housing as the collet rod is moved forwardly.

12. An automatic injection device containing a pre-loaded charge of medicament for automatically self-administering the medicament upon actuation thereof, the device comprising:
- a housing assembly having an interior chamber, the interior chamber including a dry compartment containing a dry medicament component, and a wet compartment containing a liquid component to be mixed with the dry medicament component;
- a seal structure between the dry compartment and the wet compartment, the seal structure being initially in a sealing condition that maintains the dry component sealed from the wet component, the seal structure being converted to a mixing condition as a result of activation of the device;
- the seal structure having a periphery that forms a peripheral seal slidably disposed with respect to an adjacent surface of the interior chamber, the seal structure having an inner seal portion spaced radially inward from the peripheral seal that seals a passage formed in the seal structure prior to activation of the device, the inner seal portion being convertible from a sealing condition to a mixing condition to enable fluid to flow through the passage in the seal structure;
- a needle assembly that dispenses the charge of medicament from the housing;
- an activation assembly carried by the housing and including a stored energy source, wherein activation of the activation assembly releases the stored energy from the stored energy source, and wherein the release of the stored energy causes a) the seal structure to be converted from the sealing condition to the mixing condition and thereby permit the liquid component to pass therethrough b) force the mixed liquid and dry components through the needle assembly.

13. An automatic injection device according to claim 12, wherein the inner seal portion is a burstable membrane.

14. An automatic injection device according to claim 12, further comprising a fluid distributing member disposed between the liquid component and the dry medicament component.

15. An automatic injection device according to claim 14, wherein the fluid distributing member comprises a filter.

16. An automatic injection device according to claim 14, wherein the fluid distributing member moves from an initial position spaced rearwardly from the needle assembly to a final position disposed closer to the needle assembly relative to the initial position.

17. An automatic injection device according to claim 12, wherein the seal structure moves from an initial position spaced rearwardly from the needle assembly to a final position disposed closer to the needle assembly relative to the initial position.

18. An automatic injection device according to claim 12, wherein the activation assembly includes a pre-compressed spring.

19. An automatic injection device according to claim 12, wherein the seal structure and the distributing member are integrated into a single assembly.

20. An automatic injection device according to claim 12, wherein the inner seal member is a movable plug.

21. A separation assembly for a container for separating a first component from a second component, wherein the first component is to be mixed with the dry component in the container upon occurrence of a predetermined operating condition, the separation assembly comprising:
- a generally cylindrical body that is constructed and arranged to be slidably supported within the container between the first component and the second component,
- wherein the body includes a seal structure constructed and arranged to be disposed within the container between the first component and the second component, the seal structure having an inner seal portion, the inner seal member being initially in a sealing condition that maintains the dry component sealed from the first component, the inner seal portion being converted to a mixing condition in response to the predetermined operating condition such that the first component flows through the seal structure to mix with the second component,
- wherein the body further includes a flow distributing member disposed adjacent the seal structure to evenly distribute the first component into the second component upon occurrence of the predetermined operating condition,
- whereby the seal structure and the flow distributing member form a single unit.

22. The separation assembly according to claim 21, wherein the flow distributing member comprises a filter.

23. The separation assembly according to claim 21, wherein the seal structure comprises a sealing assembly and the inner seal portion includes a burstable membrane carried by the sealing assembly.

24. The separation assembly according to claim 23, wherein the sealing assembly has an outer periphery that is constructed and arranged to form a peripheral seal with an interior wall of the container.

* * * * *